United States Patent [19]

Ninomiya et al.

[11] Patent Number: 5,028,778
[45] Date of Patent: Jul. 2, 1991

[54] SURFACE ANALYSIS METHOD AND A DEVICE THEREFOR

[75] Inventors: Ken Ninomiya, Hachioji; Shigeru Nishimatsu, Kokubunji, both of Japan

[73] Assignee: Hitachi, Ltd., Tokyo, Japan

[21] Appl. No.: 425,056

[22] Filed: Oct. 20, 1989

[30] Foreign Application Priority Data

Oct. 24, 1988 [JP] Japan ................................ 63-266037

[51] Int. Cl.$^5$ ......................................... G01N 23/227
[52] U.S. Cl. ..................................... 250/305; 250/306
[58] Field of Search ................................. 250/305, 306

[56] References Cited

U.S. PATENT DOCUMENTS 4,590,376  5/1986  Smith ............................... 250/385.1

OTHER PUBLICATIONS

J. Hermanson, J. Anderson and G. Lapeyre, "Observation of f-Band Final-State Structures in Gold by Ultraviolet Photoemission Spectroscopy", *Physical Review B*, vol. 12, No. 12, (Dec. 15, 1975), pp. 5410–5414.

T. D. Bussing and P. H. Holloway, "Deconvolution of Concentration Depth Profiles from Angle-Resolved XPS Data", *Journal of Vacuum Science & Technology A*, vol. 3, No. 3, Pt. 2, (May–Jun. 1985), pp. 1355.

C. W. Magee and R. E. Honig, "Depth Profiling by SIMS—Depth Resolution, Dynamic Range and Sensitivity", *Surface and Interface Analysis*, vol. 4, No. 2, (1982), pp. 37–41.

B. L. Henke, P. Lee, T. J. Tanaka, R. L. Shimabukuro and B. K. Fujikawa, "Low-Energy X-Ray Interaction Coefficients: Photoabsorption, Scattering and Reflection: E=100–200 eV; Z=1–94", *Atomic Data and Nuclear Data Tables*, vol. 27, No. 1, (Jan. 1982), pp. 1–22.

M. P. Seah and W. A. Dench, "Quantitative Electron Spectroscopy of Surfaces: A Standard Data Base for Electron Inelastic Mean Free Paths in Solids", *Surface and Interface Analysis*, vol. 1, No. 1, (1979), pp. 2–11.

L. Lindau and W. E. Spicer, "The Probing Depth in Photoemission and Auger-Electron Spectroscopy", *Journal of Electron Spectroscopy and Related Phenomena*, vol. 3, (1974), pp. 409–413.

J. J. Yeh and L. Lindau, "Atomic Subshell Photoionization Cross Sections and Asymmetry Parameters: $1 \leq Z \leq 103$", *Atomic Data and Nuclear Data Tables*, vol. 32, No. 1, (Jan. 1985), pp. 1–21.

*Primary Examiner*—Constantine Hannaher
*Attorney, Agent, or Firm*—Antonelli, Terry, Stout & Kraus

[57] ABSTRACT

Surface analysis method capable of obtaining depth profiles of elements and chemical bonds in a nondestructive manner and with high accuracy, which comprises irradiating light to a sample surface to be analyzed with changing its energy, detecting electrons emitted from the surface of the above sample and corresponding to a certain binding energy, and subjecting the resultant detected signal to integration transform; and constitution of a device for carrying out the method.

21 Claims, 3 Drawing Sheets

SURFACE ANALYSIS METHOD AND A DEVICE THEREFOR

BACKGROUND OF THE INVENTION

This invention relates to a surface and interface analysis technique, and in particular, it relates to a surface analysis method suitable for nondestructive and high-precision depth profile analysis, and an apparatus therefor.

With increasing packing density and decreasing film thickness of semiconductor devices, depth profile analysis (as well as small area analysis) has become very important.

Chemical state of a Si/SiO$_2$ interface determines the electric characteristic of an MOS transistor, and that of a polySi/SiO$_2$ or polySi/Si$_3$N$_4$ interface has an influence on the electric characteristic of a capacitor. The electric characteristics of transistors and capacitors can be greatly improved by these (abruption in an interface, and a distribution and change of elements and chemical bonds in the vicinity of an interface), analyzing these chemical states and feeding the results back to a production process. Also, in a photo-CDV process, the distribution of film-forming metals, such as W, Ti, etc., near the surface is very important.

In the above examples, elements and chemical bonds to be analyzed exist in a region with a depth from a sample surface of a few to several tens nm. Hence, surface analysis technique necessary for analyzing them is required to have capability of analyzing atomic species and their chemical bonds or changes in their compositions in a region from the top surface of a sample to its several tens nm deep interior part. Also, the surface analysis technique is required to achieve a depth resolution of about 0.1 nm in case that an interface abruptly changes in its structure or composition and so on. It goes without saying that the technique is required to be nondestructive.

Conventional depth profile analysis techniques are as follows. One of the well-known techniques is AES (Auger Electron Spectroscopy) or SIMS (Secondary Ion Mass Spectroscopy). These techniques carry out depth profile analysis by irradiating a sample surface with ions having a large kinetic energy for sputtering the surface, and analyzing the surface or sputtered particles. The other techniques are EDX (Energy Dispersion X-ray Spectroscopy) and PIXE (Particle Induced X-ray Emission), in which depth profile analysis is carried out by irradiating the surface with particle beams and measuring intensity attenuation caused by absorption of emitted X-ray by the sample.

The above prior techniques have the following problems.

One of the problems is cascade mixing found in an ions-sputtering method. Within a region irradiated with ions (a region from an irradiated surface to a 1 to 10 nm deep interior part), due to the above effect, element distribution tends to be uniform. Therefore, it is impossible to obtain any depth profiles in this region. In addition to this cascade mixing, the ion-sputtering method has other various factors to decrease analysis accuracy, such as a preferential sputtering caused by a difference in atomic species, crater edge effect caused by non-uniformity of ion beams, etc. As a result, the depth resolutions in AES and SIMS are limited to 1 nm [C. W. Magee and R. E. Honig, Surf. Interface Anal. 4, 35 (1982)]. Furthermore, AES and SIMS have problems that chemical bond analysis is almost impossible and that the analysis is destructive.

On the other hand, EDX and PIXE are only applicable to depth profile analysis of a sample with layered structures (an element distribution within the layer is uniform), and their depth resolution is about 5 nm. EDX and PIXE therefore have a low resolution, and furthermore, they do not make it possible to carry out depth profile analysis of elements whose distribution continuously changes.

As mentioned above, the prior art methods has a low depth resolution, and no accurate depth profiles can be measured. Furthermore, the prior art methods also have a disadvantage that the chemical bond analysis is impossible.

SUMMARY OF THE INVENTION

It is an object of this invention to provide a surface analysis method having capability of giving depth profiles of elements and chemical bonds in a nondestructive manner and with a high accuracy (depth resolution ≃ 0.1 nm).

In order to achieve the above object, this invention uses, as a surface analysis technique, photoelectron spectroscopy such as XPS (X-ray Photoelectron Spectroscopy) and UPS (Ultraviolet Photoelectron Spectroscopy). In photoelectron spectroscopy, detailed information of atomic species and chemical bonds can be obtained by irradiating a sample surface with lights (e.g. soft X rays, vacuum ultraviolet rays, etc.) and analyzing energies of electrons emitted from the sample surface.

By using this photoelectron spectroscopy, emitted electrons which always have a constant energy difference from the energy of incident light are detected with changing the energy of the incident light onto a sample surface. That is, only emitted electrons corresponding to a certain binding energy are detected in synchronization with a change in energy of the incident light. Then, signals outputted from a detector for said detection are subjected to mathematical transform (integration transform) to give an intended element depth profile.

As discussed previously, in XPS and UPS, it is possible to analyze atomic species and chemical bonds by irradiating a sample surface with lights and analyzing energy of emitted electrons. Furthermore, this analysis method is essentially nondestructive since it does not use any process such as ion sputtering.

The following will discuss a process for detecting only emitted electrons corresponding to a certain binding energy with changing the energy of incident lights, and subjecting detected signals to integration transform.

In XPS and UPS, when a binding energy is taken as $E_B$, an output signal from a detector after energy analysis carried out synchronizingly with a change in energy of incident light as I and an energy of incident light onto a sample surface as E, the following relationship exists:

$$I(E) = K \int_0^\infty n(x)\sigma(E) f(x,E) \exp\left[ - \frac{x}{\lambda(E - E_B)\cos\theta} \right] dx, \quad (1)$$

where x denotes the depth measured inwardly from a sample surface, $\theta$ denotes the angle for electron emission, and K, n, $\sigma$, f and $\lambda$ respectively denote a constant, the atomic density in the sample, the photoionization cross section of an element, the intensity of incident light and the escape depth of electrons emitted from the element (mean free path). In Eq. (I), it is supposed that the horizontal distribution of the element is uniform (this method is also effectively usable in a case where the horizontal distribution is not uniform, as will be discussed later).

When light having an energy of not less than several tens eV is taken as an incident light onto a sample surface, the reciprocal $\nu^{-1}$ of a photoabsorption coefficient $\mu$ is larger than 100 nm for most substances [B. L. Henke et al., Atomic data and nuclear data tables 27. pp. 1-144 (1982)]. Meanwhile, if $\lambda(E-E_B)$ is limited to several tens nm or less (by adjusting the energy of incident light), it can be supposed that $\mu^{-1} >> \lambda(E-E_B)$. That is, in this case, attenuation of incident light within a sample can be neglected, and Eq. (I) can be rewritten as $$G(P) = \frac{I(E)}{\sigma(E)f(E)} = \int_0^\infty [Kn(x)]e^{-px} dx, \quad (2)$$

where $$P = P(E, E_B) = 1/[\lambda(E-E_B)\cos\theta]. \quad (3)$$

In Eq. (3), it is known that $\lambda(E-E_B)$ can be approximated as $$\lambda(E-E_B) = \frac{A}{(E-E_B)^2} + B\sqrt{E-E_B} \quad (4)$$

for most substances, and the constants A and B are determined [M. P. Seah and W. A. Dench. Surf. Interface Anal. 1, 2 (1979)]Furthermore, with regard to many metal elements such as Si, Au, etc., there are exactly measured values of $\lambda$ as a function of $E-E_B$ [I. Lindau and W. E. Spicer. J. Elect. Spectrosc. Relat. Phenon. 3, 409 (1974)]. Then, if the energy E of incident light onto a sample surface is given, a value of P can be determined on the basis of the reported values and Eqs. (3) and (4).

Meanwhile, the output signal from a detector, I(E) in Eq. (2), is a measured value, and the intensity of incident light, f(E), is measurable as will be discussed in example. Furthermore, there are detailed data for the photoionization cross section $\sigma(E)$ [J. J. Yeh and I. Lindau, Atomic data and nuclear data tables 32. pp. 1-155 (1985)]. Therefore, values of G(P) can be determined for various values of P by changing the energy E of incident light onto a sample surface. That is, G(P) can be obtained as a function of P.

The integration in Eq. (2) is a type of integration transform of Kn(x) and called Laplace transform. The Laplace transform has an inverse transform (which will be also referred to as integration transform hereinbelow) represented by the following equation.

$$Kn(x) = \lim_{m\to\infty} \frac{(-1)^m}{m!}\left(\frac{m}{x}\right)^m + I_G(m)\left(\frac{m}{x}\right) \quad (5)$$

As is shown in Eq. (5), after numerical differentiation of G(P) is carried out many times up to convergence, Kn(x) can be obtained, i.e. a depth profile n(x) of the element corresponding certain binding energy $E_B$ is obtained (a value for K can be determined by usual photoelectron spectroscopy). The depth resolution in this method is about a changing interval of $\lambda$, i.e. about 0.1 nm, as is clear from Eqs. (5) and (3).

As discussed above, the present invention makes it possible to obtain the depth profiles of elements and chemical bonds with a resolution of $\approx 0.1$ nm by changing the energy of incident light onto a sample surface, detecting only electrons corresponding a certain binding energy in synchronization with the change, and subjecting output signals from a detector to integration transform. Furthermore, the method of the present invention uses light, and hence it is nondestructive.

When a distribution of elements, etc., is expected to change in the horizontal direction as well as in the lateral direction, the above method is also usable with focusing the light.

The above explanation uses the Laplace transform, but it is of course possible to use other integration transforms. Furthermore, to be more precise, correction terms, e.g. angular dependence, etc., will be taken into account in Eq. (1) to (5). However, these correction terms do not have any essential influence on the above discussion (and it should be understood that these correction terms can be considered as required).

DESCRIPTION OF PREFERRED EMBODIMENTS

Figure 1:
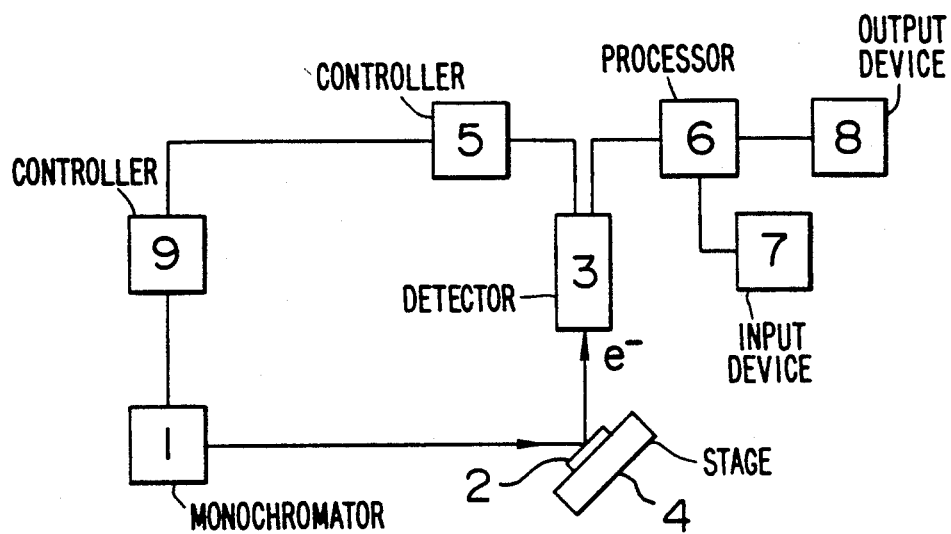
FIGS. 1 to 5 show different embodiments of the present invention.

Embodiments of the present invention will be explained by referring to the drawings and the following Examples.

EXAMPLE 1

In FIG. 1, sample 2 supported by a sample stage 4 is irradiated with light from a monochromator 1. Electrons, which are emitted from the surface of the sample 2, are energy-analyzed and detected by a detector 3. The monochromator 1 is under the control of a controller 9, whereby wavelength of incident light onto the sample 2 can be scanned. On the other hand, the detector 3 is under the control of a controller 5 synchronizing with the controller 9. As a result, with changing the wavelength of incident light onto the sample 2 (i.e. energy), it is possible to detect only emitted electrons corresponding to a certain binding energy in synchronization with the change in energy of the incident light. A signal outputted from the detector 3 is inputted into a processor 6. And a photoionization cross section $\sigma(E)$ of an element is also inputted from an input device 7 into the processor 6. (In this instance, it is supposed that the intensity f(E) of incident light described in the previous section is nearly constant in the entire range of wavelength scanned. A case where f(E) is changed will be discussed in Example 2.) On the basis of the above data, integration transform is carried out in the processor 6, and the resultant processed data, i.e. n(x), is outputted to an output device 8. The processor 6 may be one whose hardware is devised to be suitable for integration transform, or a high speed computer under the control of a software.

According to this embodiment, it is possible to measure depth profiles of certain elements and chemical bonds in a nondestructive manner and with a high accuracy (high depth resolution) by changing the wavelength of the incident light onto the sample 2, simultaneously detecting only electrons corresponding to a certain binding energy in synchronization with the change and subjecting the detected signals to integration transform.

EXAMPLE 2

In Example 1, it has been supposed that f(E) is nearly constant in the entire range of wavelength. This Example 2 describes a case where f(E) is changed in the range of wavelength scanned.

Figure 2:
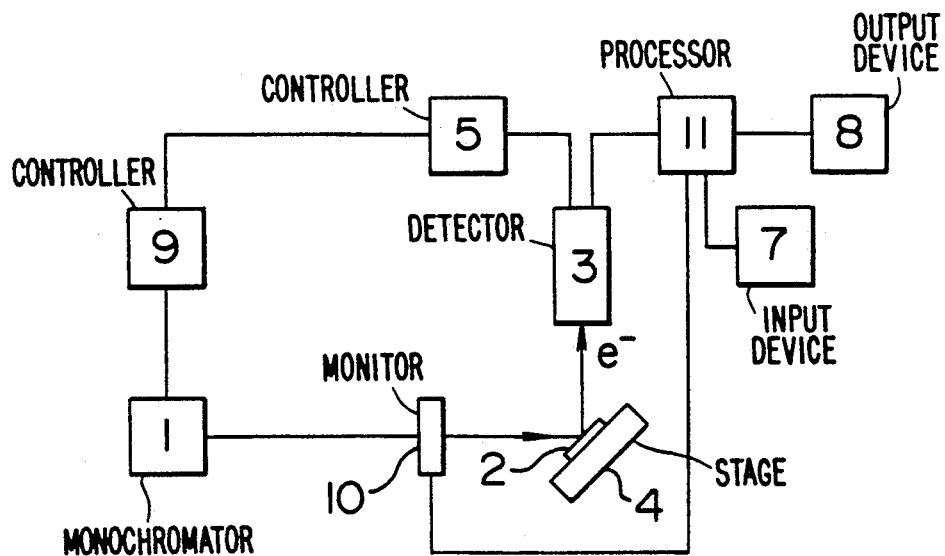

FIG. 2 shows a constitution of a device therefor. The different point of the device in this Example 2 from that of Example 1 is that a monitor 10 for measuring the intensity of incident light is provided between a monochromator 1 and a sample 2. Light from the monochromator 1 is transmitted through the monitor 10 and then to the sample 2. A light intensity signal from the monitor 10 (e.g. an electric current signal by secondary electron emission resulting from light irradiation) is inputted into a processor 11. In the processor 11, changes in intensity of incident light onto the sample 2 and photoionization cross section of the elements are taken into account in integration transform according to the processing step discussed in the previous section. The resultant processed data is outputted into an output device 8.

According to this embodiment, it is possible to determine an exact depth profile even if the intensity of incident light onto the sample 2 is changed, since the change is corrected.

EXAMPLE 3

In the foregoing Examples, it has been supposed that the element distribution in the horizontal direction within the sample 2 is uniform. However, some samples have a non-uniform element distribution in the horizontal direction. In such a case, in order to determine the depth profile of the element, it is necessary to focus an incident light within a small area on the sample surface.

Figure 3:
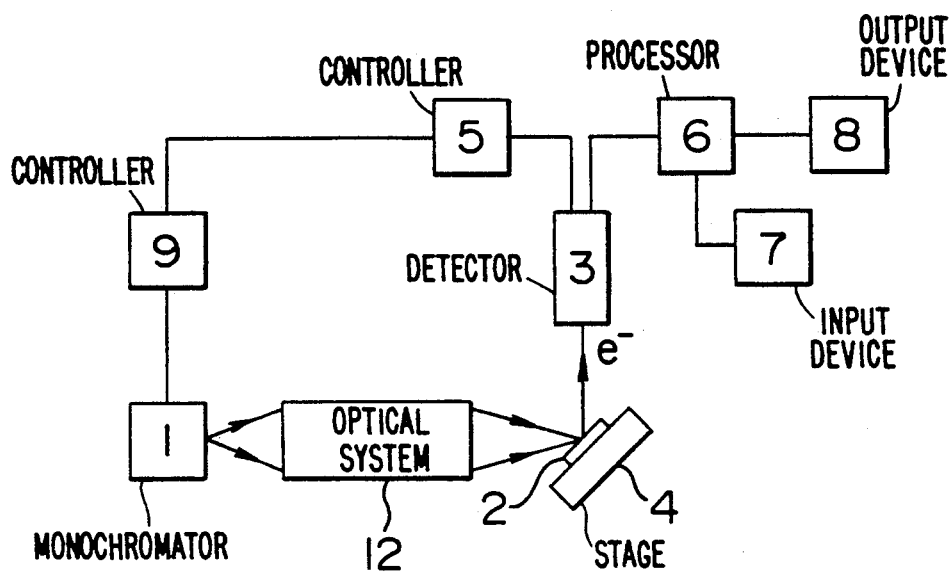

FIG. 3 shows an embodiment for such a case. Light from a monochromator 1 is focused, with an optical system 12, within a small area on the surface of a sample 2. Electrons emitted from the surface by light irradiation are energy-analyzed and detected by a detector 3. The other portions are the same as those in Example 1.

In this case, the optical system 12 is desirably a combination of mirrors using total reflection. XPS and UPS use the light ranging from soft X-ray to vacuum ultraviolet regions. The lights in the above region can be focused by using a system of transmission-diffraction or mirror optics. In the mirror optical system, optical characteristics such as focal distance do not change even if the wavelength is changed. Therefore, mirror optical systems are suitable for the present invention. The system of transmission-diffraction optics is also usable if a displacement mechanism for the sample 2, corresponding to changes in focal distance, and a fine adjustment mechanism for the optical system 12 are provided, although these mechanisms are not shown in FIG. 3.

According to this embodiment, an accurate depth profiles of elements can be obtained even if the sample has element distributions in the horizontal direction, since light is focused within small area.

EXAMPLE 4

Figure 4:
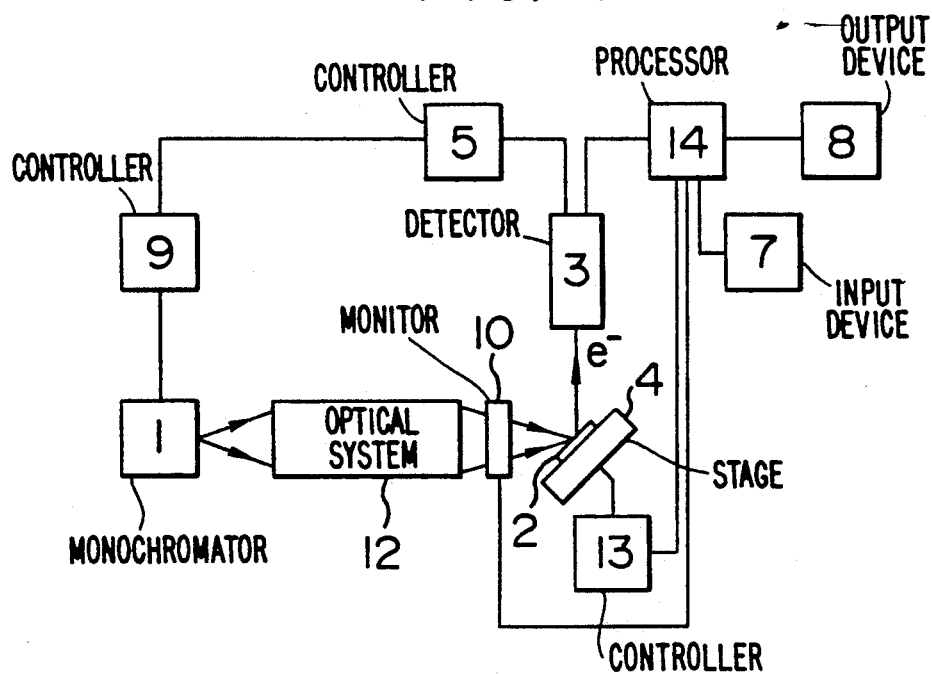

FIG. 4 shows one embodiment for a device to obtain three-dimensional distributions of elements and chemical bonds. The largest different point of the device of this Example from that of Example 3 is that a controller 13 permits fine displacement of a sample stage 4. A signal on the displacement of a sample is inputted from the controller 13 to a processor 14.

In this embodiment, a depth profile can be obtained by a change in wavelength of incident light and integration transform, and a distribution in the horizontal direction by fine displacement of a sample. These two obtained data are combined to give a three-dimensional distribution of an element.

EXAMPLE 5

Figure 5:
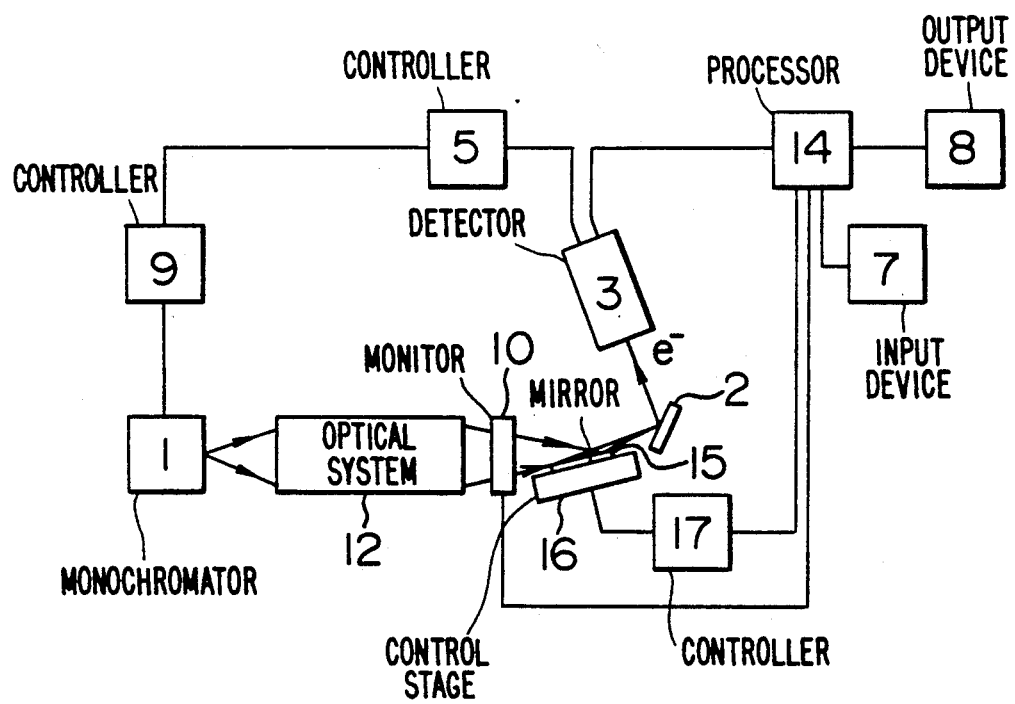

In Example 4, a distribution in the horizontal direction is obtained by fine displacement of the sample stage 4 (i.e. a sample). However, a distribution in the horizontal direction can be also obtained by some other methods. FIG. 5 shows one embodiment therefor.

In FIG. 5, light is reflected on a reflection mirror 15. In this case, scanning the light beams on the surface of a sample 2 is possible by changing the angle and position of a control stage 16, on which the reflection mirror 15 is placed, by a controller 17 with a high accuracy. A signal on the changes of angle and position of the control stage 16 is inputted from the controller 17 to a processor 14 as a signal of scanning the light beam.

According to this embodiment, it is possible to obtain the same three-dimensional distribution as that of Example 4 since scanning the light beam is carried out with the reflection mirror 15.

The essence of Examples 4 and 5 is a change of the light irradiated position on the surface of the sample 2. The light irradiated position can be also changed by some other methods than those shown in these Examples. The present invention also includes a method to obtain a three-dimentional distribution by using such other methods.

In the foregoing Examples, adjustment of the incident angle of the light onto a sample and the angle of electron detection (an angle between the axis of the detector 3 and the surface normal of a sample) makes it possible to carry out the analysis with a higher depth resolution. In order to make clear the essence of the present invention, however, mechanisms for the adjustments of these angles have not shown in FIGS. 1 to 5. It should therefore be understood that these angle adjustment mechanisms can be supplied as required.

The light source for the monochromator 1 is required to have a wide wavelength range. For example, synchrotron radiation and bremsstrahlung in a X-ray tube can be considered as such.

As discussed in detail above, in the present invention, while the energy of incident light onto a sample surface is changed, only electrons corresponding to a certain binding energy are detected in synchronization with the change, and the detected signals are subjected to integration transform. It is therefore possible to obtain depth profiles of elements and chemical bonds in a nondestructive manner and with a high accuracy. Furthermore, when incident light is focused on the sample surface and allowed to be scanned it is possible to obtain three-dimensional distributions of elements and chemical bonds.

What is claimed is:

1. A surface analysis method which comprises irradiating light to a surface of a sample with changing its energy, detecting a signal of only electrons emitted from the surface of the sample and corresponding to a certain binding energy, and subjecting the resultant detected signal to integration transform.

2. A surface analysis method according to claim 1 wherein the integration transform is Laplace transform.

3. A surface analysis method according to claim 1 wherein the integration transform is integration transform in which a change of photoionization cross section of an element accompanying a change of energy of incident light to the sample, a change of intensity of the incident light or these two changes are taken into account.

4. A surface analysis method according to claim 1 wherein the light is in the soft X-ray to vacuum ultraviolet regions.

5. A surface analysis method according to claim 1 wherein the light is focused on a certain region on the the sample surface.

6. A surface analysis method according to claim 5 wherein the light is focused by using a mirror optics, a transmission-diffraction optics or both of these.

7. A surface analysis method according to claim 5 wherein the sample is displaced with controlling its position relative to the axis of the light.

8. A surface analysis method according to claim 5 wherein the light is scanned on the sample surface.

9. A surface analysis method according to claim 1, wherein the detecting of a signal of only electrons emitted from the surface of the sample and corresponding to a certain binding energy is effected in synchronization with the change of energy of the irradiating light, the integration transform enabling a depth composition profile of the sample.

10. A surface analysis method which comprises irradiating light to a surface of a sample with changing its energy, detecting a signal of only electrons which are emitted from the surface of the sample and have a constant energy difference from the energy of the light, and subjecting the resultant detected signal to integration transform.

11. A surface analysis method according to claim 10, wherein the detecting of a signal of only electrons which are emitted from the surface of the sample and have a constant energy difference from the energy of the light is effected in synchronization with the change of energy of the light, the integration transform enabling a depth composition profile of the sample.

12. A surface analysis device for observation of electrons emitted from a sample surface by light irradiation to the sample surface, which comprises means of changing the energy of the light, energy analysis means of the emitted electrons in synchronization with an energy change of the light, detection means of energy-analyzed electrons, and integration-transform means of an electron-detected signal.

13. A surface analysis device according to claim 12 wherein the integration-transform means is means of carrying out Laplace transform.

14. A surface analysis device according to claim 12 wherein the integration-transform means has means of inputting a change of photoionization cross section accompanying a change of energy of the incident light onto the sample, or it has monitoring means of a change of intensity of the incident light accompanying the change of energy of the incident light, and means of inputting the monitor intensity signal.

15. A surface analysis device according to any of the preceding claims 12 to 14 wherein the light is in the soft X-rays to vacuum ultraviolet regions.

16. A surface analysis device according to claim 12 which has means of focusing the light on a certain region on the sample surface.

17. A surface analysis device according to claim 16 wherein the means for focusing the light comprises a system of mirror optics, a system of transmission-diffraction optics or both of these.

18. A surface analysis device according to claim 16 which has means of displacing the sample to a designated position relative to the axis of the light.

19. A surface analysis device according to claim 16 which has means of scanning the light on the sample surface.

20. A surface analysis device according to claim 16 the means of scanning is means using the reflection of the light on a mirror surface.

21. A surface analysis device according to claim 12, wherein the energy analysis means and the detecting means enable detection of a signal of only electrons emitted from the surface of the sample and corresponding to a certain binding energy in synchronization with the energy change of the light, the integration-transform means enabling a depth composition profile of the sample.

* * * * *